United States Patent [19]
Joffe

[11] Patent Number: 5,925,024
[45] Date of Patent: *Jul. 20, 1999

[54] SUCTION DEVICE WITH JET BOOST

[76] Inventor: Michael A Joffe, 25 Alderbrook Ct., Wrentham, Mass. 02093

[*] Notice: This patent is subject to a terminal disclaimer.

[21] Appl. No.: 08/858,817

[22] Filed: May 19, 1997

Related U.S. Application Data

[63] Continuation-in-part of application No. 08/601,327, Feb. 16, 1996, Pat. No. 5,630,807.

[51] Int. Cl.$^6$ ..................................................... A61M 1/00
[52] U.S. Cl. ............................................. 604/313; 604/315
[58] Field of Search ..................................... 604/289, 290, 604/291, 313, 315, 316, 317, 319, 320; 55/385.1, 467; 134/7; 128/303.1, 747

[56] References Cited

U.S. PATENT DOCUMENTS

| | | | |
|---|---|---|---|
| 4,450,756 | 5/1984 | Kling | 55/467 |
| 4,735,603 | 4/1988 | Goddson et al. | 604/317 |
| 4,758,217 | 7/1988 | Gueret | 604/49 |
| 4,921,492 | 5/1990 | Schultz et al. | 604/315 |
| 4,963,134 | 10/1990 | Backscheider et al. | 55/467 |
| 5,009,685 | 4/1991 | Wilson | 55/467 |
| 5,015,243 | 5/1991 | Schifano | 604/315 |
| 5,047,072 | 9/1991 | Wertz et al. | 604/317 |
| 5,062,898 | 11/1991 | McDermott et al. | 134/7 |
| 5,125,979 | 6/1992 | Swain et al. | 134/7 |
| 5,294,261 | 3/1994 | McDermott et al. | 134/7 |
| 5,322,521 | 6/1994 | Wilk | 604/317 |
| 5,366,156 | 11/1994 | Bauer et al. | 239/135 |
| 5,516,505 | 5/1996 | McDow | 604/291 |
| 5,630,807 | 5/1997 | Joffe | 604/315 |

*Primary Examiner*—John G. Weiss
*Assistant Examiner*—David J. Cho
*Attorney, Agent, or Firm*—John R. Ross; John R. Ross, III

[57] ABSTRACT

A device for evacuating plume products. A gas is forced through at least one compressed gas jet nozzle which directs a compressed gas flow toward an evacuation orifice. A vacuum system provides a vacuum at said evacuation orifice sufficient to provide a vacuum mass flow rate substantially greater than said compressed gas mass flow rate so that the plume products are entrained in gas exiting said gas jet nozzles and evacuated along with the gas through the evacuation orifice. In one embodiment, compressed gas may be cooled to produce aerosol particles to further improve collection efficiency and produce beneficial therapeutic effects. The device is especially useful in laser surgery to evacuate ablation products in plumes created by pulse lasers.

10 Claims, 4 Drawing Sheets

SUCTION DEVICE WITH JET BOOST

This is a continuation-in-part application of Ser. No. 08/601,327, filed Feb. 16, 1996, now U.S. Pat. No. 5,630,807. This invention relates to suction devices and in particular to suction devices for use in laser surgery.

BACKGROUND OF THE INVENTION

When lasers are used in surgery, tissue is often ablated producing smoke and vaporized tissue. This smoke and vaporized tissue is potentially dangerous and can contaminate delicate medical equipment. It is standard practice for an assistant to the surgeon to remove the products of the ablation with a suction device. Laser plumes consist of microscopic particles flying ballistically away from the irradiated tissue surface. The idea of suction, as shown in FIG. 1A, is to impart to the plume particle a velocity component parallel to the surface in the direction of the suction nozzle so that it can be captured inside a suction nozzle. The larger the horizontal velocity component, the more efficient suction is. A 5 $\mu$m diameter, $5\times10^{-10}$ gm particle, initially flying ballistically vertically with a velocity V and subject to a horizontal wind U, will have a trajectory roughly equal to:

$$z = (0.1)V\frac{x}{U},$$

where z and x are respectively the particle's vertical and horizontal components.

FIG. 1B shows plots of a the trajectory of the 5 $\mu$m particle assuming a 100 cm/s initial velocity for 5 different horizontal wind velocities.

In order to remove all of the products of ablation, the mouth of a suction device typically must be held close to the location of the surgery; however, use of the suction device close to the surgery area can be disruptive to the surgery.

SUMMARY OF THE INVENTION

The present invention provides a device for evacuating plume products. A gas is forced through at least one compressed gas jet nozzle which directs a compressed gas flow toward an evacuation orifice. A vacuum system provides a vacuum at said evacuation orifice sufficient to provide a vacuum mass flow rate substantially greater than said compressed gas mass flow rate so that the plume products are entrained in gas exiting said gas jet nozzles and evacuated along with the gas through the evacuation orifice. In one embodiment, compressed gas may be cooled to produce aerosol particles to further improve collection efficiency and produce beneficial therapeutic effects. The device is especially useful in laser surgery to evacuate ablation products in plumes created by pulse lasers.

DETAILED DESCRIPTION OF PREFERRED EMBODIMENTS

Preferred embodiments of the present invention can be described by reference to the drawings.

Figure 1A:
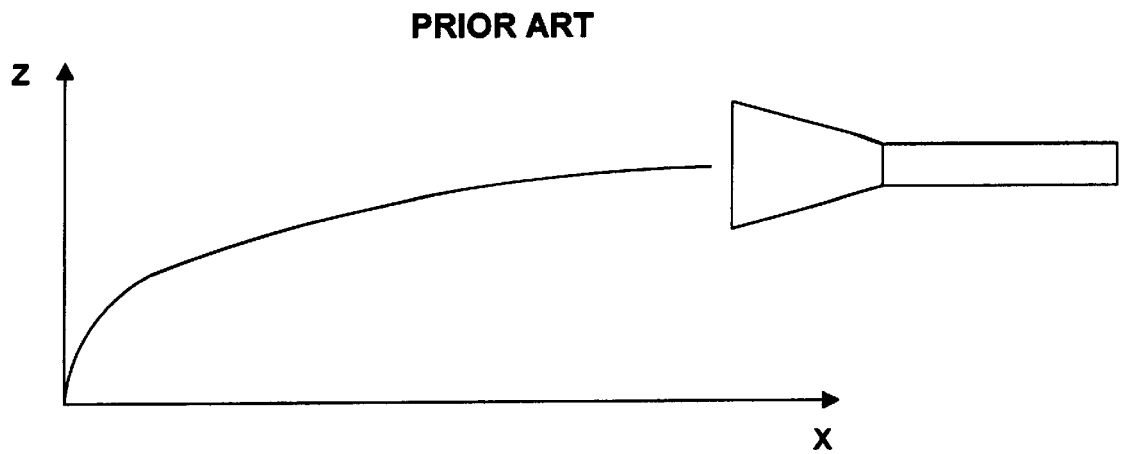
FIG. 1A illustrates typical prior art suction devices.
Figure 1B:
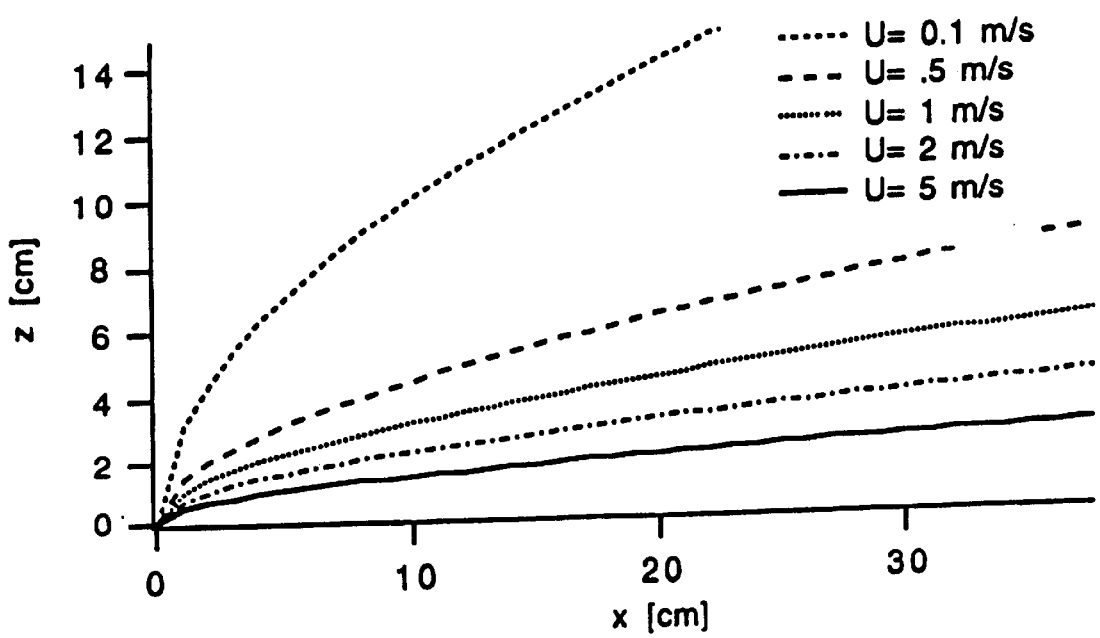
FIG. 1B shows a plot of a typical plume particle subject to various horizontal winds.

As can be seen from FIG. 1B, in order for the trajectory of the plotted particles to end inside a typical 1 cm sized nozzle located 10 cm away, the wind velocity has to exceed 5 m/s. It is impossible to achieve this air flow with suction nozzles. Typical suction velocities are in the range of 0.25 to 0.75 m/s. However, it is very easy to create air velocities of 5 m/s with a blower or compressed air.

Preferred Embodiments

Figure 3:
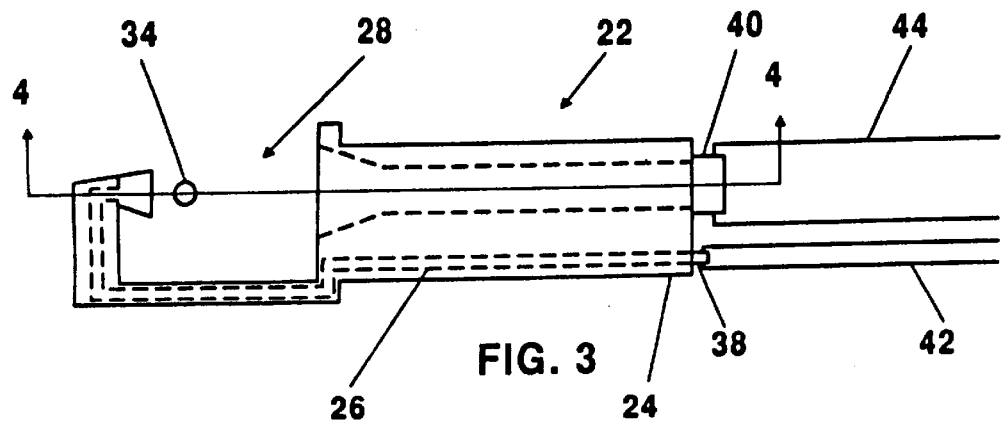
FIG. 3 shows the top elevation of the elements of a preferred embodiment of the present invention.
Figure 4:
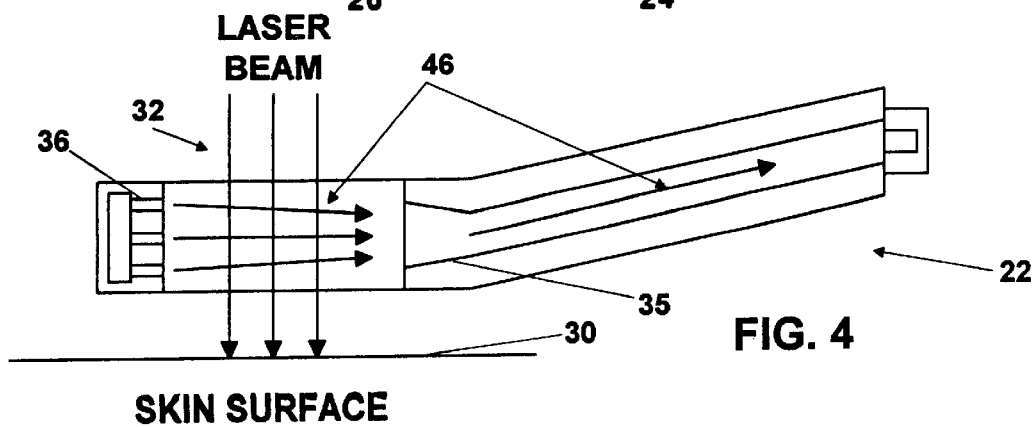
FIG. 4 shows the side elevation of the elements of a preferred embodiment of the present invention.

A preferred embodiment of a suction device 22 with a jet spray is shown in FIGS. 3 and 4. A handle 24 provides a compressed air passage 26 for incoming compressed air and an exhaust passage for evacuation of the compressed air and a laser created plume. Suction device 22 provides an illumination space 28 through which skin surface 30 is illuminated by laser beam 32 at spot 34. The plume created by the ablation of skin tissue is blown toward evacuation nozzle 35 by compressed air exiting at high speed from 12 compressed air jet nozzles 36, each directing compressed air in the direction of the center of evacuation nozzle 35.

Suction device 22 is comprised of molded plastic with standard fittings 38 and 40 to accommodate flexible compressed air hose 42 and flexible vacuum hose 44. A compressor (e.g. Gast Model 1531-107B-G557X) with a regulator capable of providing compressed air at about 1–5 liter/min at about 100 psi is connected to the suction device with hose 42. Compressed air enters device 22 through fitting 38 and exits through 12 jet nozzles 36, each about 0.5 mm diameter. Air exits nozzles 36 with velocity of about 20 m/s, which is sufficient for imparting significant drag force to plume particles created by laser pulses 32 at spot 34. Actual pressure and flow are adjustable, with higher air velocity required for higher power and short-pulse lasers. The air path is shown at 46.

Evacuation hose 44 with an inside diameter of about 1 inch connects the device to a vacuum pump such as Gast Model R2103. Sufficient air moving capacity insures that the jet flow from nozzles 36 is only a small fraction of the total air flow through hose 44. Evacuation nozzle 46 is 4 cm high and 2.5 cm wide. Applicant's experiments have shown that essentially all plume particles and smoke are caught up in the compressed air flow and evacuated through exhaust nozzle 35.

In another preferred embodiment the suction device is incorporated as a feature of the laser optic at the terminal of a laser articulated arm or a fiber-optic-coupled handpiece. This permits the laser practitioner to operate without an assistant.

Cooling Compressed Gas

Figure 5:
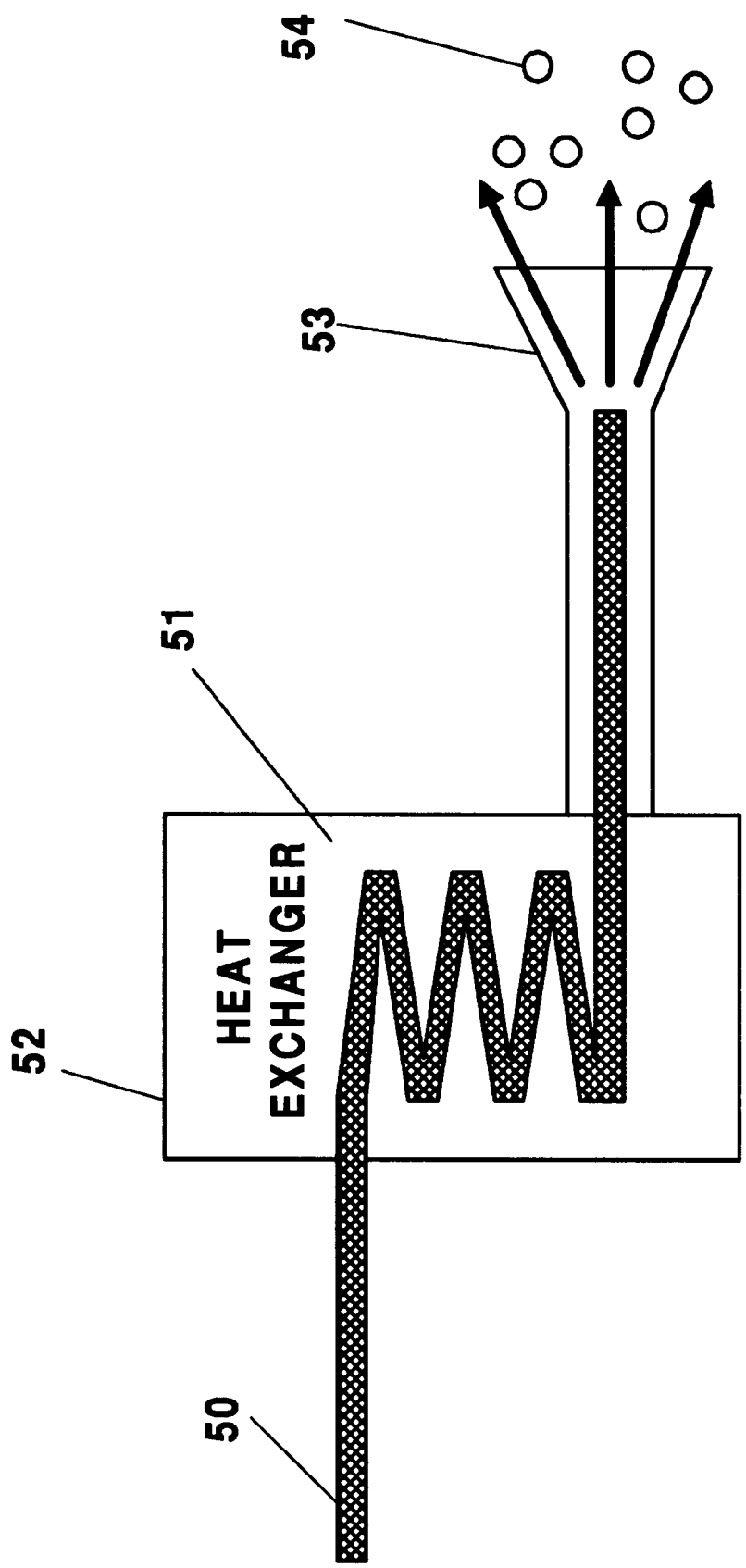
FIG. 5 shows a principle of cooling and aerosol generation in the jet.

Another preferred embodiment can be described by reference to FIG. 5. The laser surgery device may be improved by cooling the compressed gas. Cooling the compressed gas has several benefits. By proper choice of the gas and the degree of cooling, portions of the gas can be forced to condense into small droplets or freeze into small particles. These droplets or particles are aerosols as indicated in FIG. 5. Cooling the compressed gas prior to it contacting the skin generates a cool mist of aerosol particles due to moisture condensation. The presence of the cool aerosol particles in the jet stream improves momentum transfer to plume particles as well as providing an anesthetic effect on the skin.

Presence of aerosol particles in the jet stream further improves momentum transfer to plume particles. In addition to viscous drag force caused by jet stream these heavier-than-air particles have masses comparable with plume particles, so that they collide with plume particles and efficiently transfer lateral momentum to them thus knocking them towards a suction nozzle. In all of these embodiments utilizing aerosol particles, the effect on the laser beam must be considered and it might be necessary to increase the energy in the laser beam. If the compressed gas is pulsed, the laser beam could be synchronized to precede the compressed gas pulse by a very short time period.

First the compressed gas 50 is chilled by external refrigeration 51 in heat exchanger 52 prior to entering the jet nozzle 53, as shown in FIG. 5. Then, compressed gas 50 is further cooled by adiabatic expansion through jet nozzle 53. Cooling of expanding compressed gas is well known as the Joule-Thompson effect whereby a drop in pressure of compressed gas escaping through a nozzle causes a drop in the gas temperature. Cooling can easily be achieved for most common gases such as air, nitrogen, argon, carbon dioxide, and freon. Substantial cooling can cause freezing to produce "snow flakes" 54. These snow flakes melt and evaporate on the skin surface efficiently cooling the skin. Cooling compressed air could also generate mist due to moisture condensation. The following U.S. patents disclose methods of creating aerosols in various compressed gases: U.S. Pat. Nos. 5,294,261; 5,125,979; 5,366,156 and 5,062,898. The teachings of these patents are incorporated herein by reference.

Demonstrations

Figure 2:
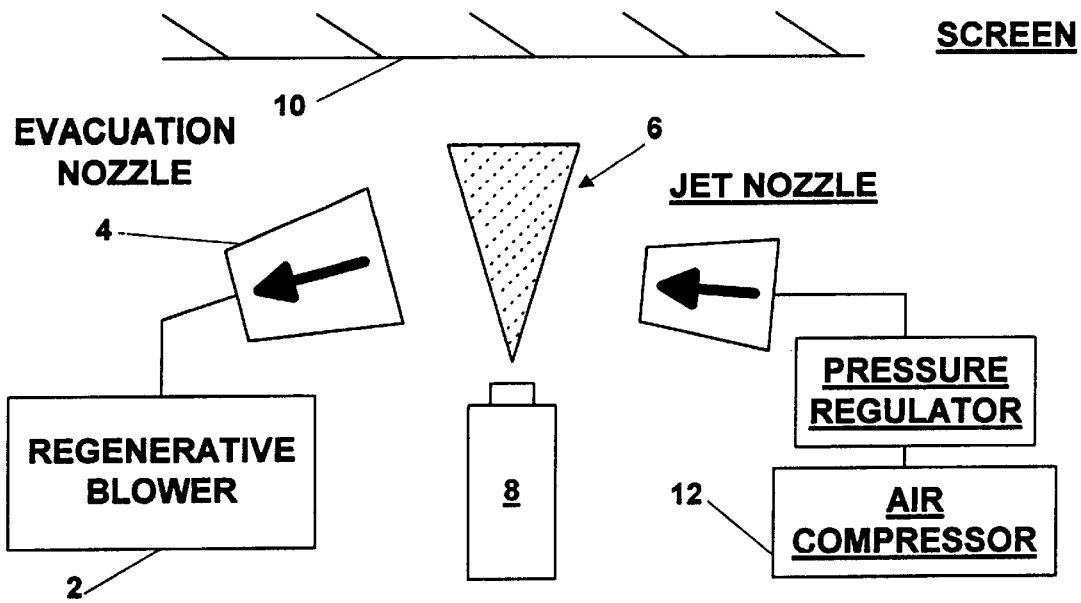
FIG. 2 shows the elements of a demonstration of the principals of the present invention.
Figure 6:
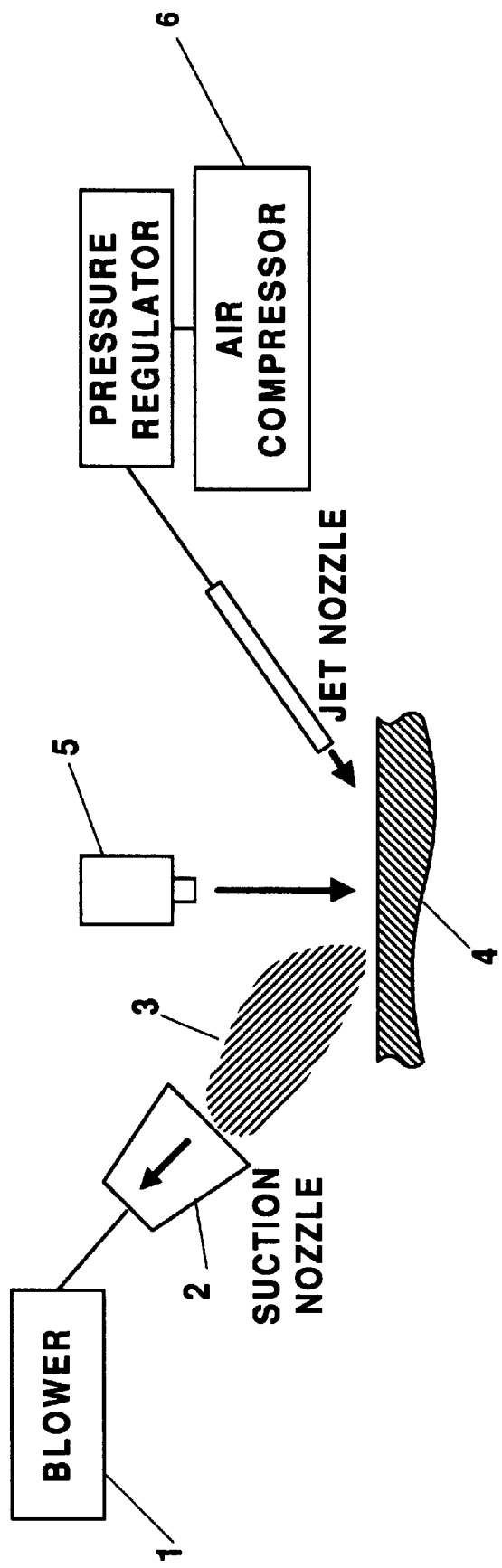
FIG. 6 shows the elements of a second demonstration of the principals of the present invention.

I conducted two simple demonstrations to illustrate the principles of my invention. The elements of the demonstrations are shown in FIGS. 2 and 6. The first demonstration is illustrated in FIG. 2. Blower 2 with suction nozzle 4 was completely ineffective in preventing paint spray plume 6 from paint spray can 8 from reaching screen 10. However, when compressed air from air compressor 12 was directed at spray plume 6 in the direction of suction nozzle 4, essentially all of the spray was sucked into suction nozzle 4 and none of the spray reached screen 10.

The second demonstration is illustrated in FIG. 6. Initially, Blower 1 (manufactured by Buffalo Filter Inc. with offices in East Amherst, N.Y.) with suction nozzle 2 was ineffective in completely evacuating smoke plume 3 from red meat tissue 4 irradiated by a 100 W cw CO2 laser 5 (Coherent). However, when compressed air from air compressor 6 was directed at smoke plume 3 in the direction of suction nozzle 2, all of the spray appeared to be sucked into suction nozzle 2. Approximately 2 lpm of compressed air created local air velocity in excess of 20 m/s which appeared to be sufficient for capturing all the smoke.

While the above description contains many specificities, the reader should not construe these as limitations on the scope of the invention, but merely as exemplifications of embodiments thereof. Those skilled in the art will envision many other possible variations which are within its scope. For example instead of a compressor, compressed gas in a compressed gas bottle can be used to provide the compressed gas to the compressed gas jet nozzle. Several jet nozzles could be provided with all of the nozzles focused on the evacuation nozzle. The present invention may in addition to laser surgery be used to capture laser plumes from non-medical procedures, e.g. laser micromachining, laser cutting, etc. The present invention may also be used to capture debris such as those resulting from non-laser plume creating procedures such as welding, soldering, drilling, milling, lathing, and brazing. A jet flow used to boost collection efficiency can be used in continuous or pulsed mode. The continuous jet described in the preferred embodiment could instead be pulsed and synchronized with the laser pulse to save compressed air, reduce suction requirements and increase collection efficiency by means of a shock wave front. Compressed air gas described in the preferred embodiments can be further replaced by chemically inert gas, such as compressed nitrogen. Thus produced inert atmosphere around the irradiated spot eliminates production of hazardous free radicals and their oxidation products in laser plume. These byproducts of tissue burning during laser therapy have been shown to be carcinogenic. In another further embodiment, the jet stream is seeded with fine cool aerosol particles produced by an external source. In another embodiment a disinfecting agent can be added to the compressed gas to help eliminate microorganisms in the plume. Also a deodorizing agent could be added to reduce odors. A built-in filter can be added to the suction portion of the device. A tank or other appropriate accumulator could be provided for accumulation of the plume products. Alternately, the plume products could be directed outdoors when this is permitted. With appropriate arrangement of piping, filter and waste accumulator tank a single compressor could be used to provide both compressed gas for the jet nozzle and the suction for the suction orifice. Accordingly, the reader is requested to determine the scope of the invention by the appended claims and their legal equivalents and not by the examples which have been given.

I claim:

1. A plume suction device for evacuating plume products produced in an open air operation comprising:

A) at least one evacuation orifice,

B) at least one compressed gas jet nozzle spaced apart from said at least one evacuation orifice and located so as to direct compressed gas toward said evacuation orifice, C) a compressed gas source means for providing compressed gas flow defining a compressed gas mass flow rate to said at least one compressed gas jet nozzle, D) a suction means for providing a vacuum mass flow rate through said evacuation orifice substantially greater than said compressed gas mass flow rate, and E) a cooling means to cool said compressed gas.

2. The plume suction device as in claim 1, wherein at least fifty percent of said compressed gas comprises at least one gas chosen from the following group of gases: argon, carbon dioxide and freon.

3. The plume suction device as in claim 1, wherein said at least one compressed gas nozzle is configured to cause cooling of said compressed gas through adiabatic expansion.

4. The plume suction device as in claim 1, wherein said cooling means comprises a jet nozzle configured to produce aerosols by cooling said compressed gas through adiabatic expansion.

5. The plume suction device as in claim 1, wherein said cooling means comprises a heat exchanger for cooling said compressed gas prior to said gas reaching said nozzle.

6. The plume suction device as in claim 2, wherein said compressed gas is cryogenic.

7. A method for evacuating plume products in an open air operation, said method comprising the steps of:

A) positioning at least one evacuation orifice at a first side of a plume location, B) positioning at least one compressed gas jet nozzle at a second side of said plume location spaced apart from said at least one evacuation orifice so as to direct compressed gas toward said plume location and said evacuation orifice, C) providing a compressed gas flow, defining a compressed gas mass flow rate, to said at least one compressed gas jet nozzle, wherein said compressed gas comprises aerosol particles, and wherein said compressed gas is cooled, D) providing a suction flow to produce a vacuum mass flow rate through said at least one evacuation orifice substantially greater than said compressed gas mass flow rate, and E) creating a plume at said plume location, so that the products of said plume are entrained in gas exiting said gas jet nozzle and evacuated along with said gas through said evacuation orifice.

8. A method as in claim 7, wherein said cooling of said gas is achieved by passing said compressed gas through a heat exchanger.

9. A method as in claim 7, wherein said aerosol particles are produced by adiabatic cooling of said compressed gas by a jet nozzle configured to cooling by adiabatic expansion.

10. A method as in claim 7, and comprising the steps of externally producing aerosol particles and then adding them to said compressed gas mass flow rate.

* * * * *